United States Patent [19]
Lochead et al.

[11] Patent Number: 6,143,761
[45] Date of Patent: Nov. 7, 2000

[54] 2,3-DIHYDROFURO [3,2-β]PYRIDIN, PREPARATION AND APPLICATION THEREOF IN THERAPY

[75] Inventors: Alistair Lochead, Charenton; Samir Jegham, Argenteuil; Frédéric Galli, Vaucresson; Thierry Gallet, Palaiseau, all of France

[73] Assignee: Sanofi-Synthelabo, Paris, France

[21] Appl. No.: 09/381,098

[22] PCT Filed: Mar. 17, 1998

[86] PCT No.: PCT/FR98/00531

§ 371 Date: Sep. 15, 1999

§ 102(e) Date: Sep. 15, 1999

[87] PCT Pub. No.: WO98/42713

PCT Pub. Date: Oct. 1, 1998

[30] Foreign Application Priority Data

Mar. 20, 1997 [FR] France ................... 97 03395

[51] Int. Cl.[7] ............. A61K 31/435; C07D 491/048
[52] U.S. Cl. ................ 514/302; 546/115; 546/116
[58] Field of Search ................... 546/115, 116; 514/302

[56] References Cited

FOREIGN PATENT DOCUMENTS

WO 97/05139  2/1997  WIPO .

*Primary Examiner*—Bernard Dentz
*Attorney, Agent, or Firm*—Finnegan, Henderson, Farabow, Garrett, & Dunner, L.L.P.

[57] ABSTRACT

Compounds corresponding to the general formula (I)

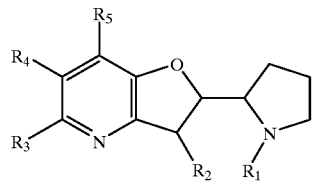

(I)

in which $R_1$ represents a hydrogen atom, a $(C_1-C_6)$alkyl group or a phenyl$(C_1-C_4)$alkyl group, $R_2$ represents a hydrogen atom or a $(C_1-C_6)$alkyl group and $R_3$, $R_4$ and $R_5$ each represent, independently of one another, a hydrogen or halogen atom or a trifluoromethyl, cyano, hydroxyl, $(C_1-C_6)$alkyl or $(C_1-C_6)$alkoxy group. Application in therapeutics.

9 Claims, No Drawings

2,3-DIHYDROFURO [3,2-β]PYRIDIN, PREPARATION AND APPLICATION THEREOF IN THERAPY

This application is a 371 of PCT/FR98/00531 filed Mar. 17, 1998.

The subject of the present patent application is 2,3-dihydrofuro[3,2-b]pyridine derivatives, their preparation and their application in therapeutics.

The compounds of the invention correspond to the general formula (I)

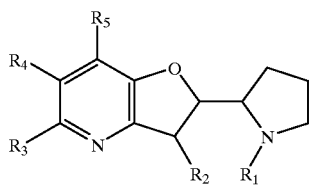

in which

R₁ represents a hydrogen atom, a (C₁–C₆)alkyl group or a phenyl(C₁–C₄)alkyl group which is optionally substituted, R₂ represents a hydrogen a tom or a (C₁–C₆)alkyl group, and R₃, R₄ and R₅ each represent, independently of one another, a hydrogen or halogen atom or a trifluoromethyl, cyano, hydroxyl, (C₁–C₆)alkyl or (C₁–C₆)alkoxy group.

The two carbon atoms by which the pyrrolidine ring and the furo[3,2-b]pyridine ring are bonded are asymmetric; a compound according to the invention can thus exist in the form of a pure (R,R), (R,S), (S,R) or (S,S) optical isomer or of a mixture of such isomers.

A compound according to the invention can also exist in the form of the free base or of an addition salt with an acid.

Compounds having structures and properties similar to those of the compounds of the invention are disclosed in international application WO-9705139.

Advantageous compounds are those in which R₁ and R₂ each represent a hydrogen atom or an alkyl group, preferably a methyl group, and R₃, R₄ and R₅ each represent a hydrogen or halogen atom, preferably chlorine, or a (C₁–C₄) alkyl, preferably methyl, or (C₁–C₄)alkoxy, preferably methoxy, group.

Scheme 3

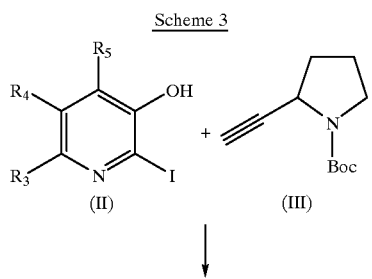

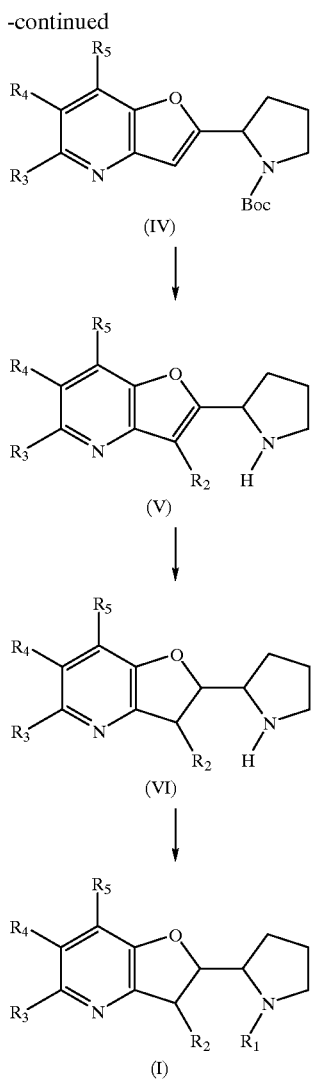

In accordance with the invention, the compounds of general formula (I) can be prepared by a process illustrated by the above scheme.

A 2-halopyridin-3-ol of general formula (II), in which R₃, R₄ and R₅ are as defined above and X represents a halogen atom, is first reacted with 1,1-dimethylethyl 2-ethynylpyrrolidine-1-carboxylate of formula (III), under the conditions of a Castro-Stephens reaction, as described in *J. Org. Chem.* (1966), 31, 4071, or else in the presence of copper(I), as described in *Synthesis* (1986), 749–751, in order to obtain the cyclized derivative of general formula (IV). For some compounds, not all the R₃, R₄ and R₅ substituents may be present from the beginning of the synthesis; in these cases, their introduction can be carried out starting from the compound of general formula (IV), in which R₃, R₄ and R₅ each represent a hydrogen atom, according to any known method, for example that described in *J. Het. Chem.* (1996), 33, 1051–1056, optionally after activation of the nitrogen of the pyridine ring by formation of the corresponding N-oxide. The nitrogen of the pyrrolidine ring is subsequently deprotected in order to obtain the compound of general formula (V). The latter is subjected to catalytic hydrogenation in order to obtain the compound of general formula (VI) and finally, and if desired, the nitrogen of the pyrrolidine ring is alkylated by any known method, for example a methylation according to the Eschweiler-Clarke method (formaldehyde and formic acid) or by a reductive amination in the presence of an aldehyde and of sodium cyanoborohydride, or alternatively is acylated in order to form an amide, followed by a reduction in the presence of a reducing agent, such as lithium aluminium hydride.

The 2-halopyridin-3-ols are commercially available or can be prepared according to any method known to a person skilled in the art.

1,1-Dimethylethyl (S)-2-ethynylpyrrolidine-1-carboxylate and 1,1-dimethylethyl (R)-2-ethynylpyrrolidine-1-carboxylate can be prepared from (S)- or (R)-proline by the Corey-Fuchs method described in *Tetrahedron Letters* (1990), 31, (28), 3957–3960.

The examples which will follow illustrate the preparation of some compounds of the invention. The elemental microanalyses and the I.R. and N.M.R. spectra confirm the structures of the compounds obtained. The numbers shown between brackets in the titles of the examples correspond to those in the 1st column in Table 1 given later.

In the names of the compounds, the "—" forms part of the word and the "_" is used only for the break at the line end; it is to be omitted in the absence of a break and should not be replaced either by a normal hyphen or by a space.

EXAMPLE 1

(Compounds No. 1 and 2).

Diastereoisomers of (2S)-2-(pyrrolidin-2-yl)-2,3-dihydrofuro[3,2-b]pyridine.

1.1. 1,1-Dimethylethyl (S)-2-(furo[3,2-b]pyridin-2-yl)pyrrolidine-1-carboxylate.

2.0 g (10.24 mmol) of 1,1-dimethylethyl (S)-2-ethynyl-1-pyrrolidinecarboxylate and 2.26 g (10.24 mmol) of 2-iodopyridin-3-ol are dissolved in 50 ml of pyridine, under an argon atmosphere, in a 100 ml three-necked round-bottomed flask. 0.88 g (6.15 mmol) of copper(I) oxide is added and the mixture is heated at reflux for 24 h.

The solution is filtered through paper and the solvent is evaporated under reduced pressure. The residue is purified by chromatography on silica gel, elution being carried out with a 60/40 and then 50/50 mixture of cyclohexane and ethyl acetate.

2.43 g of product are thus obtained in the form of a thick oil.

$[\alpha]_D^{20}=-102.6°$ (c=1, CHCl$_3$).

1.2. (S)-2-(Pyrrolidin-2-yl)furo[3,2-b]pyridine dihydrochloride.

2.25 g (7.80 mmol) of 1,1-dimethylethyl (S)-2-(furo[3,2-b]pyridin-2-yl)pyrrolidine-1-carboxylate are dissolved in 20 ml of dichloromethane in a 100 ml round-bottomed flask and 17.8 ml (0.156 mol) of trifluoroacetic acid are added. Gas is given off. After stirring for 24 h, the solvent is evaporated, the residue is taken up in water and the solution obtained is basified by addition of a concentrated aqueous sodium hydroxide solution. Extraction is carried out with dichloromethane in order to obtain the crude product in the form of an oil, which product is purified by chromatography on silica gel, elution being carried out with a 95/5/0.5 mixture of dichloromethane, ethanol and aqueous ammonia, in order to obtain the pure product in the form of the base.

The hydrochloride is formed by addition of hydrochloric acid in ethanol.

1.35 g of product are thus obtained.

Melting point: 174–175°

$[\alpha]_D^{20}=-9°$ (c=1, CH$_3$OH).

1.3. Diastereoisomers of (2S)-2-(pyrrolidin-2-yl)-2,3-dihydrofuro[3,2-b]pyridine.

6.0 g (22.97 mmol) of (S)-2-(pyrrolidin-2-yl)furo[3,2-b]pyridine dihydrochloride are introduced into 400 ml of ethanol in a 1 l three-necked round-bottomed flask. 3 g of 10% palladium-on-charcoal are added and catalytic hydrogenation is carried out for 10 h.

The catalyst is removed by filtration, the solvent is evaporated under reduced pressure and the products of the reaction are purified by chromatography on silica gel, elution being carried out with a 96/4/0.4 mixture of dichloromethane, ethanol and aqueous ammonia. 0.22 g of the least polar diastereoisomer (Compound No. 1) is thus obtained in the form of the base.

Melting point: 79–81° C., $[\alpha]_D^{20}=+63.7°$ (c=1, CHCl$_3$), and 1.2 g of the most polar diastereoisomer (Compound No. 2) are thus obtained in the form of the base. The latter is dissolved in ethanol and treatment is carried out with a solution of hydrochloric acid in ethanol in order to obtain, after crystallization from butanone, 1.56 g of product in the dihydrochloride form.

Melting point: 171–173°, $[\alpha]_D^{20}=-75.9°$ (c=1, CH$_3$OH).

EXAMPLE 2

(Compound No. 6).

(−)-(2S)-2-(1-Methylpyrrolidin-2-yl)-2,3-dihydrofuro[3,2-b]pyridine tartrate.

0.6 g (2.19 mmol) of the most polar diastereoisomer of (2S)-2-(pyrrolidin-2-yl)-2,3-dihydrofuro[3,2-b]pyridine dihydrochloride obtained during the preceding stage is dissolved in 100 ml of ethanol in a 250 ml round-bottomed flask and then 250 µl (4.38 mmol) of acetic acid and 3.55 ml (4.38 mmol) of a 37% aqueous formaldehyde solution are added. The mixture is cooled to 0° C., 0.275 g (4.38 mmol) of sodium cyanoborohydride is added and the mixture is stirred for 3 h. The solvent is evaporated under reduced pressure and the mixture is basified by addition of concentrated aqueous ammonia. The solution obtained is evaporated and the residue is purified by chromatography on a column of silica gel, elution being carried out with a 90/10/1 mixture of dichloromethane, ethanol and aqueous ammonia, in order to obtain the product in the form of the base. The latter is taken up in ethanol and 0.235 g of tartaric acid is added. After evaporation of the solvent under reduced pressure, 0.70 g of product is obtained in the form of a hygroscopic solid.

Melting point: 70–71° C.

$[\alpha]_D^{20}=-107.3°$ (c=1, H$_2$O).

The chemical structures and the physical properties of some compounds of the invention are illustrated in the following table.

TABLE (I)

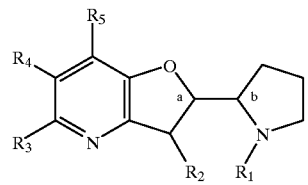

| No. | R$_1$ | R$_2$ | R$_3$ | R$_4$ | R$_5$ | b | Salt | M.p. (° C.) | $[\alpha]_D^{20}$ (°) |
|---|---|---|---|---|---|---|---|---|---|
| 1 | H | H | H | H | H | S | — | 79–81 | +63.7 (c = 1, CHCl$_3$) |

TABLE-continued

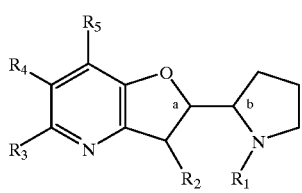

(I)

| No. | $R_1$ | $R_2$ | $R_3$ | $R_4$ | $R_5$ | b | Salt | M.p. (° C.) | $[\alpha]_D^{20}$ (°) |
|---|---|---|---|---|---|---|---|---|---|
| 2 | H | H | H | H | H | S | 2HCl | 171–173 | −75.9 (c = 1, CH$_3$OH) |
| 3 | H | H | H | H | H | R | — | 75–76 | −62.7 (c = 1, CHCl$_3$) |
| 4 | H | H | H | H | H | R | Tar. | 69–70 | +26.5 (c = 0.65, H$_2$O) |
| 5 | CH$_3$ | H | H | H | H | S | Tar. | 56–58 | +0.7 (c = 0.7, H$_2$O) |
| 6 | CH$_3$ | H | H | H | H | S | Tar. | 70–71 | −107.3 (c = 1, H$_2$O) |
| 7 | CH$_3$ | H | H | H | H | R | Tar. | 56–58 | −28.3 (c = 1, H$_2$O) |
| 8 | CH$_3$ | H | H | H | H | R | Tar. | 82–84 | −79.3 (c = 1, H$_2$O) |

For all the compounds, the configuration of the atom labelled "a" is either R or S but has not been determined; the configurations of the atom labelled "b" in the above formula are shown in the "b" column. In the "Salt" column, "—" denotes a compound in the form of the base, 2HCl denotes a dihydrochloride and "Tar." denotes a D-tartrate.

The compounds of the invention have formed the subject of tests which have demonstrated their therapeutic properties.

Thus, they have been studied as regards their affinity with respect to nicotinic receptors according to the methods described by Anderson and Arneric, *Eur. J. Pharmacol* (1994), 253, 261, and by Hall et al., *Brain Res.* (1993), 600, 127.

Male Sprague-Dawley rats weighing 150 to 200 g are decapitated and the entire brain quickly removed, homogenized in 15 volumes of a 0.32M sucrose solution at 4° C. and then centrifuged at 1000 g for 10 min. The pellet is discarded and the supernatant is centrifuged at 20,000 g for 20 min at 4° C. The pellet is recovered and homogenized using a Polytron® mill in 15 volumes of doubly-distilled water at 4° C., and then centrifuged at 8000 g for 20 min. The pellet is discarded and the supernatant and the layer of skin (buffy coat) are centrifuged at 4000 g for 20 min, the pellet is recovered, washed with doubly-distilled water at 4° C. and centrifuged once more before being stored at −80° C. On the day of the experiment, the tissue is slowly defrosted and suspended in 3 volumes of buffer. 150 μl of this membrane suspension are incubated at 4° C. for 120 min in the presence of 100 μl of 1 nM [$^3$H]cytisine in a final volume of 500 μl of buffer, in the presence or in the absence of test compound. The reaction is halted by filtering through Whatman GF/B® filters treated beforehand with polyethyleneimine, the filters are rinsed with two times 5 ml of buffer at 4° C. and the radioactivity retained on the filter is measured by liquid scintigraphy. The non-specific binding is determined in the presence of 10 μM (−)-nicotine; the non-specific binding represents 75 to 85% of the total binding recovered on the filter. For each concentration of compound studied, the percentage of inhibition of the specific binding of [$^3$H]cytisine is determined and then the IC$_{50}$, the concentration of compound which inhibits the specific binding by 50%, is calculated. The IC$_{50}$, values of the compounds of the invention lie between 0.01 and 100 μM.

The results of the biological tests carried out on the compounds of the invention show that they are powerful and selective cholinergic ligands for the nicotinic receptors.

These results suggest the use of the compounds in the treatment or the prevention of disorders related to dysfunctioning of the nicotinic receptors, in particular in the central nervous system or the gastrointestinal system.

In the central nervous system, these disorders comprise detrimental cognitive changes, more specifically detrimental memory changes but also detrimental attentional changes, related to Alzheimer's disease, to pathological ageing (Age Associated Memory Impairment, AAMI), to parkinsonian syndrome, to trisomy 21 (Down's syndrome), to Korsakoff's alcohol syndrome or to vascular dementias (multi-infarct dementia, MID).

The compounds of the invention can also be used in the treatment of motor disorders observed in Parkinson's disease or other neurological diseases, such as Huntington's chorea, Tourette's syndrome, tardive dyskinesia and hyperkinesia.

The compounds of the invention can also constitute a curative or symptomatic treatment of strokes and cerebral hypoxic episodes.

They can be used in cases of psychiatric pathologies: schizophrenia, depression, anxiety, panic attacks or compulsive and obsessional behaviour.

They can prevent symptoms due to withdrawal from tobacco, from alcohol or from various dependence-inducing substances, such as cocaine, LSD, cannabis or benzodiazepines.

Finally, they may be of use in the treatment of pain.

In the gastrointestinal system, the compounds of the invention could be of use in the treatment of Crohn's disease, of ulcerative colitis, of irritable bowel syndrome and of obesity.

To this end, the compounds of the invention can be presented in all composition forms appropriate for enteral, parenteral or transdermal administration, such as tablets, including sugar-coated tablets, capsules, including hard gelatin capsules, oral or injectable suspensions or solutions, such as syrups or phials, patches, and the like, in combination with suitable excipients and containing doses which allow a daily administration of 0.01 to 20 mg/kg.

What is claimed is:

1. A compound of general formula (I):

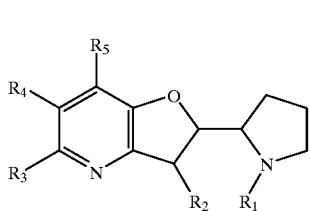

(I)

in which $R_1$ represents a hydrogen atom, a ($C_1$–$C_6$) alkyl group or a phenyl ($C_1$–$C_4$) alkyl group, $R_2$ represents a hydrogen atom, and $R_3$, $R_4$ and $R_5$ each represent, independently of one another, a hydrogen or halogen atom or a trifluoromethyl, cyano, hydroxyl, ($C_1$–$C_6$) alkyl, or ($C_1$–$C_6$) alkoxy group;

or a pure optical isomer thereof, a mixture of such isomers, or a base or an acid-addition salt thereof.

2. The compound according to claim 1, wherein $R_1$ represents a hydrogen atom or an alkyl group and $R_3$, $R_4$ and $R_5$ each represent, independently of one another, a hydrogen or halogen atom or a ($C_1$–$C_4$) alkyl, or ($C_1$–$C_4$) alkoxy group.

3. The compound according to claim 1, wherein $R_1$ represents a hydrogen atom or a methyl group and $R_3$, $R_4$ and $R_5$ each represent, independently of one another, a hydrogen or chlorine atom or a methyl or methoxy group.

4. A process for preparing a compound according to claim 1, comprising:

(a) reacting a 2-halopyridin-3-ol of general formula (II),

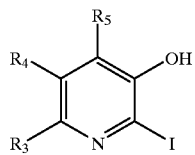

(II)

in which $R_3$, $R_4$ and $R_5$ are defined in claim 1 and X represents a halogen atom, with 1,1-dimethylethyl 2-ethynylpyrrolidine-1-carboxylate to obtain a cyclized derivative of general formula (IV)

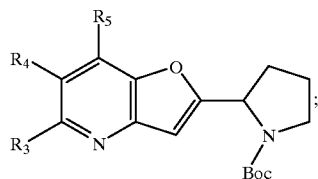

(IV)

(b) optionally modifying one or more of $R_3$, $R_4$ and $R_5$ to yield another cyclized derivative of general formula (IV);

(c) deprotecting the nitrogen of the pyrrolidine ring to obtain a compound of general formula (V):

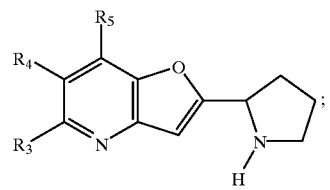

(V)

(d) subjecting the compound of general formula (V) to catalytic hydrogenation to obtain a compound of general formula (VI):

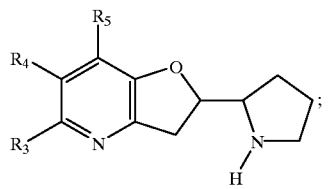

(VI)

5. A pharmaceutical composition, comprising at least one compound of claim 1 and at least one suitable excipient.

6. A method for treating or preventing a disorder related to dysfunctioning of nicotinic receptors in a human or animal patient, comprising administering to the patient in need of said treatment or prevention an amount effective of a compound of claim 1.

7. The method according to claim 6, wherein said disorder is Alzheimer's disease, pathological ageing, Parkinsonian syndrome, trisomy 21, Korsakoffs alcohol syndrome, vascular dementia, Huntington's chorea, Tourette's syndrome, tardive dyskinesia, hyperkinesia, stroke, cerebral hypoxic episode, schizophrenia, depression, anxiety, panic attack, compulsive and obsessional behavior, withdrawal, or pain.

8. The method according to claim 7, wherein said withdrawal is from tobacco, alcohol, cocaine, LSD, cannabis, or a benzodiazepine.

9. The method according to claim 6, wherein said disorder is Crohn's disease, ulcerative colitis, irritable bowel syndrome, or obesity.

* * * * *

UNITED STATES PATENT AND TRADEMARK OFFICE
CERTIFICATE OF CORRECTION

PATENT NO. : 6,143,761
DATED : November 7, 2000
INVENTOR(S) : Lochead et al.

It is certified that error appears in the above-identified patent and that said Letters Patent is hereby corrected as shown below:

Column 7, claim 1,
Line 7, after "isomers,", delete "or a base".

Column 8, claim 4,
Immediately after the structure for formula (VI), insert the following two lines:

-- and (e) optionally alkylating the nitrogen of the pyrrolidine ring.--.

Column 8, claim 7,
Line 35, "Korsakoffs" should read -- Korsakoff's --.

Signed and Sealed this

Twenty-third Day of October, 2001

Attest:

NICHOLAS P. GODICI
*Attesting Officer*     *Acting Director of the United States Patent and Trademark Office*